US00PP29793P3

(12) United States Plant Patent
Leis et al.

(10) Patent No.: US PP29,793 P3
(45) Date of Patent: Nov. 6, 2018

(54) STRAWBERRY PLANT NAMED 'CIVN260'

(50) Latin Name: ***Fragaria ananassa* Duch.**
Varietal Denomination: CIVN260

(71) Applicant: C.I.V.—CONSORZIO ITALIANO VIVAISTI—SOCIETÀ CONSORTILE A R.L., Comacchio FE (IT)

(72) Inventors: Michelangelo Leis, Ferrara (IT); Alessio Martinelli, Ferrara (IT)

(73) Assignee: C.I.V.—CONSORZIO ITALIANO VIVAISTI—SOCIETÀ CONSORTILE A R.L., Comacchio FE (IT)

( * ) Notice: Subject to any disclaimer, the term of this patent is extended or adjusted under 35 U.S.C. 154(b) by 0 days.

(21) Appl. No.: 15/731,441

(22) Filed: Jun. 12, 2017

(65) Prior Publication Data

US 2018/0042155 P1 Feb. 8, 2018

(51) Int. Cl.
*A01H 5/08* (2018.01)
*A01H 6/74* (2018.01)

(52) U.S. Cl.
USPC ..... Plt./208
CPC ..... *A01H 6/7409* (2018.05); *A01H 5/08* (2013.01); *A01H 5/0893* (2013.01)

(58) Field of Classification Search
USPC ..... Plt./208, 209
See application file for complete search history.

*Primary Examiner* — Susan McCormick Ewoldt
(74) *Attorney, Agent, or Firm* — Foley & Lardner LLP

(57) ABSTRACT

This invention relates to a new and distinct variety of strawberry plant named 'CIVN260'. This new strawberry plant named 'CIVN260' is primarily adapted high chill growing conditions, and is primarily characterized by its plants with erect leaves and visible, easy to collect fruits; fruits with regular and conical shape; easy pollination; excellent consistency; and great taste with high sugar content and aroma.

4 Drawing Sheets

Latin name of the genus and species of the plant claimed: *Fragaria ananassa* Duch.

Variety denomination: 'CIVN260'.

BACKGROUND OF THE INVENTION

The present invention relates to a new and distinct strawberry variety named 'CIVN260'. The variety is botanically known as *Fragaria ananassa* Duch.

The new strawberry 'CIVN260' is a product of a planned breeding program conducted by the inventors, Michelangelo Leis and Alessio Martinelli in San Giuseppe di Comacchio, Ferrara, Italy. The objective of the breeding program is to develop a new strawberry variety with high resistance to powdery mildew and general resistance to leaf and root disease; fruits with regular and conical shape; bright color; excellent consistency; and good taste and aroma even at high temperatures.

This new strawberry 'CIVN260' is a result of a controlled cross made by the inventors in 2009, in San Giuseppe di Comacchio, Ferrara, Italy. The female or seed parent is strawberry variety designated 'NABILA' (Patented, U.S. Plant Pat. No. 23,338). The male or pollen parent is strawberry variety designated 'CLERY' (Protected, CPVO Grant No. 16743).

The new strawberry 'CIVN260' was discovered and selected by the inventors as a single flowering plant within the progeny of the stated cross in May 2011 in San Giuseppe di Comacchio, Ferrara, Italy (44° 45' North and 12° 11' East). After its selection, the new variety was asexually propagated by stolons in a nursery located in San Giuseppe di Comacchio, Ferrara, Italy. The new variety was extensively tested over the next several years in different European area with high chill conditions. This propagation has demonstrated that the combination of combination of characteristics as herein disclosed for the new cultivar are firmly fixed and retained through successive generations of asexual reproduction. The new cultivar reproduces true to type.

BRIEF SUMMARY OF THE INVENTION

'CIVN260' is primarily adapted to the climate and growing with high chill conditions. This area provides the needed correct temperatures for flower induction and to produce a strong and vigorous plant and maintain fruit quality during fall production.

The following traits have been repeatedly observed and are determined to be unique characteristics of 'CIVN260', which in combination distinguish this strawberry plant as a new and distinct variety:

1. plants with erect leaves and visible fruits;
2. easy to collect;
3. fruits with regular and conical shape;
4. easy to pollinate;
5. excellent consistency; and
6. great taste with high sugar content and aroma.

Plants of the new strawberry variety 'CIVN260' differ from plants of the parents, 'NABILA' and 'CLERY'. in the characteristics described in Table 1.

TABLE 1

| Comparison with parent varieties | | | |
|---|---|---|---|
| Characteristic | 'CIVN260' | 'NABILA' | 'CLERY' |
| Time of ripening | Very early to early | Medium | Very early to early |
| Grow habit | Upright | Upright | Semi-upright |
| Plant vigour | Strong | Medium | Medium to strong |
| Fruit size | Large to very large | Large | Large |
| Firmness | Strong | Firm | Medium |
| Sweetness | Higher | Medium to high | Medium |

Of the many commercial cultivars known to the present inventor, the most similar in comparison to the new strawberry variety 'CIVN260' is the male parent variety 'CLERY'. Plants of the new strawberry variety 'CIVN260' differ from plants of 'CLERY' in the characteristics described in Table 2:

TABLE 2

| Comparison with Similar Variety | | |
|---|---|---|
| Characteristic | 'CIVN260' | 'CLERY' |
| Grow habit | Upright | Semi-upright |
| Plant vigour | Strong | Medium to strong |
| Fruit size | Large to very large | Large |
| Firmness | Strong | Medium |
| Sweetness | Higher | Medium |

BRIEF DESCRIPTIONS OF THE PHOTOGRAPHS

The accompanying color photographs illustrate the overall appearance of typical specimens of the new strawberry variety 'CIVN260', at various stages of development as true as it is reasonably possible with color reproductions of this type. Color in the photographs may differ slightly from the color value cited in the botanical description which accurately describe the color of 'CIVN260'. The depicted plant and plant parts of the new strawberry variety 'CIVN260' were taken in San Giuseppe di Comacchio, Ferrara, Italy, and are approximately 6 to 9 months old.

DETAILED BOTANICAL DESCRIPTION

Figure 1:
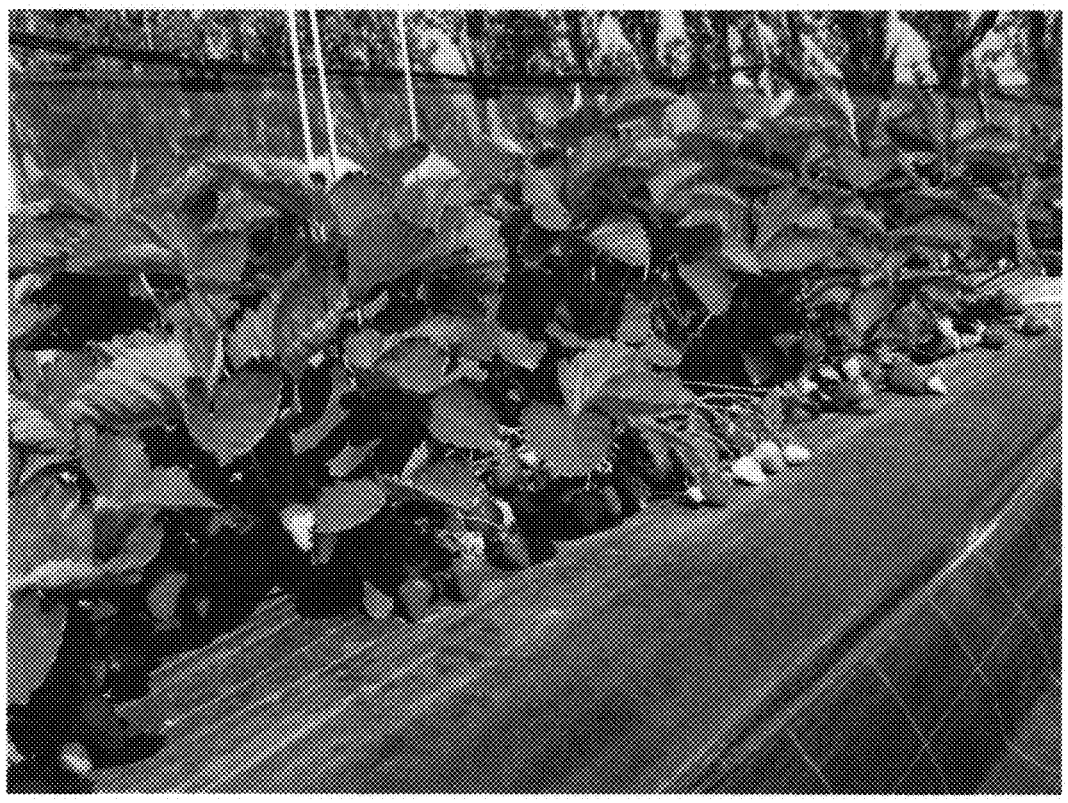
FIG. 1 shows typical plants of 'CIVN260'.
Figure 2:
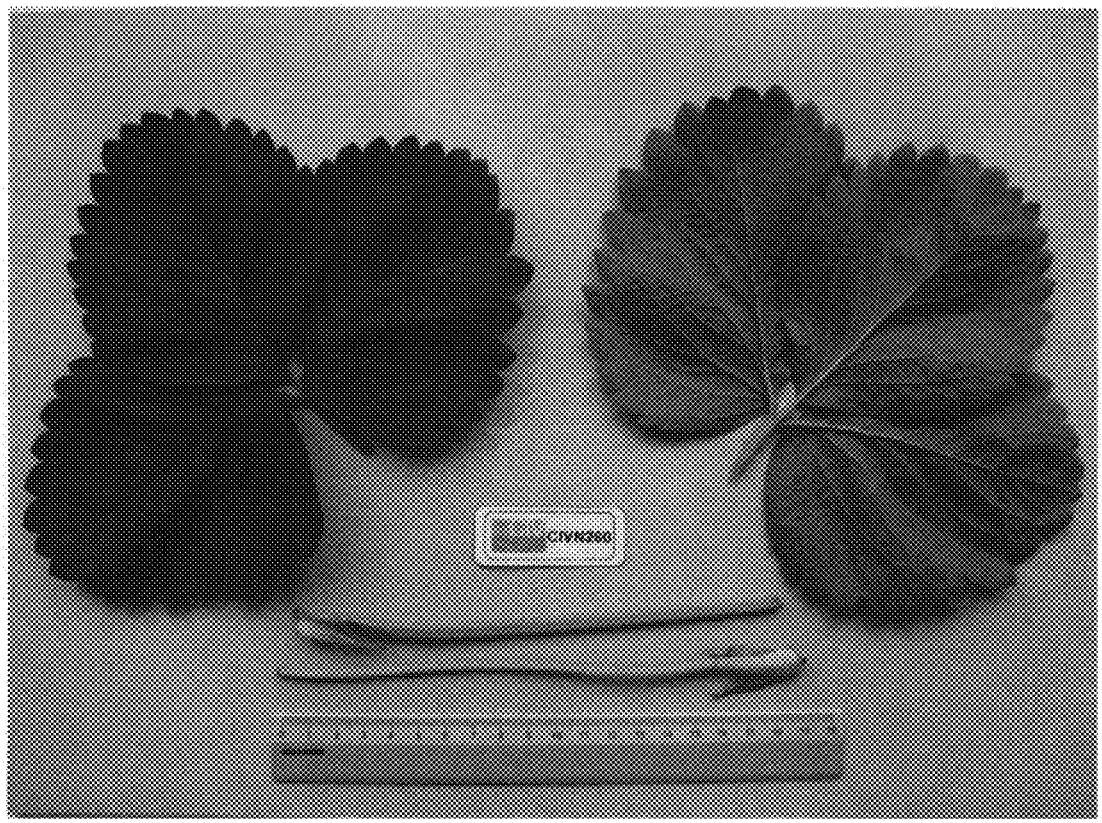
FIG. 2 shows typical leaves of 'CIVN260'.
Figure 3:
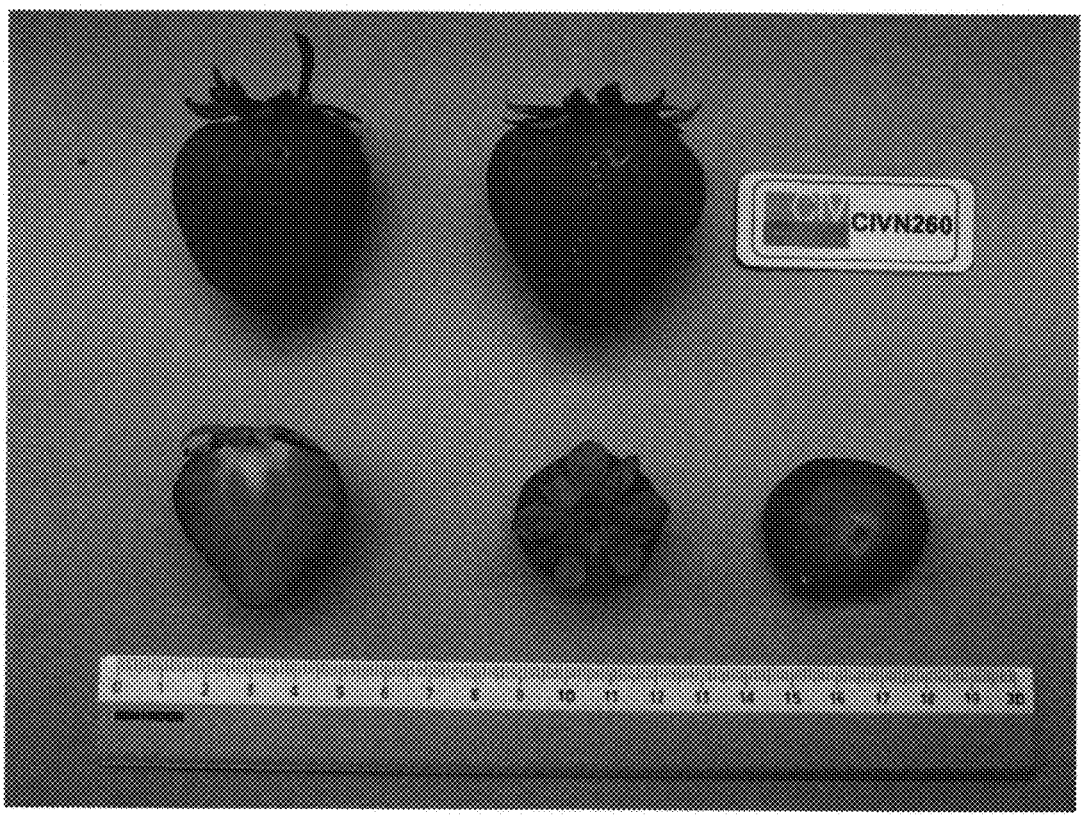
FIG. 3 shows typical fruits of 'CIVN260'.
Figure 4:
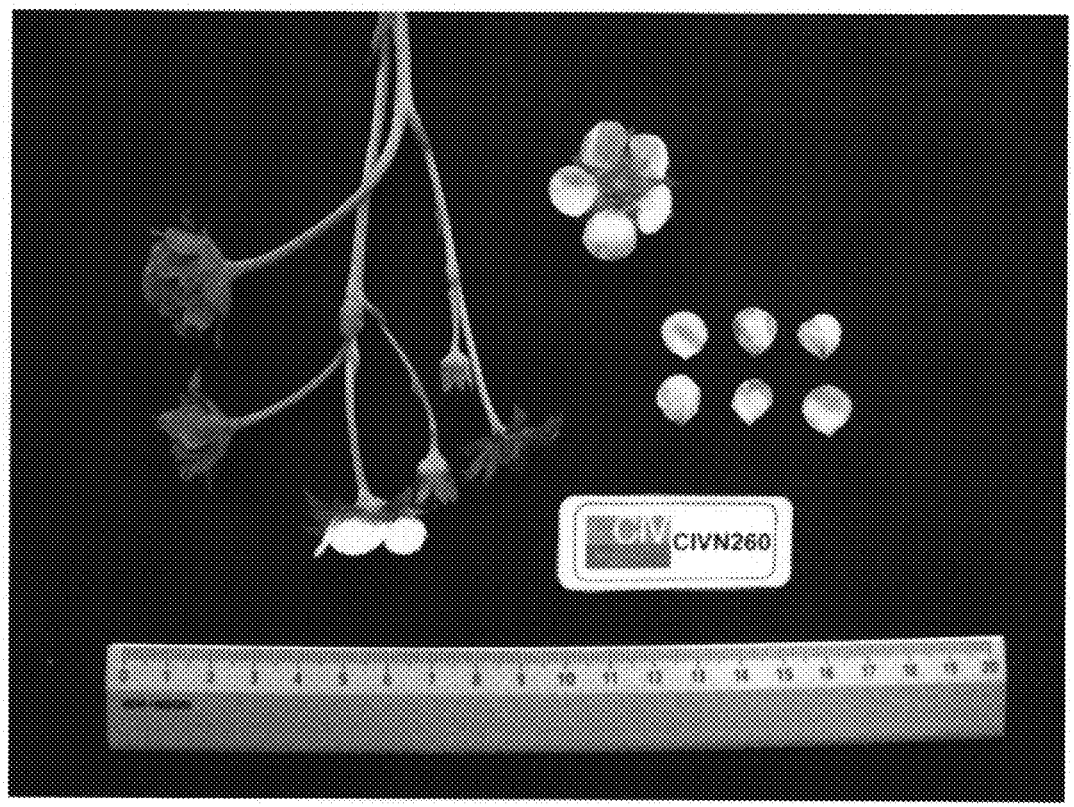
FIG. 4 shows typical flowers of 'CIVN260'.

'CIVN260' has not been observed under all possible environmental conditions. The characteristics of the new variety may vary in detail, depending upon variations in environmental factors, including weather (temperature, humidity and light intensity), day length, soil type and location.

The aforementioned photographs, together with the following observations, measurements and values describe the new strawberry variety 'CIVN260', unless otherwise noted, taken during the 2016 growing season in San Giuseppe di Comacchio, Ferrara, Italy. The observations, measurements and values were taken from plants of 'CIVN260' dug from a sea level-elevation nursery located in San Giuseppe di Comacchio, Ferrara, Italy, during January 2015 and planted approximately 7 months later in San Giuseppe di Comacchio, Ferrara, Italy. Plants of the new strawberry variety 'CIVN260' were grown under conditions which closely approximate those generally used in commercial practice.

The observed plants were one year old plants. The plants used in the production field are produced in a nursery in San Giuseppe di Comacchio.

Yield observations and fruit quality characteristics are averaged from 3 years of data collected from the 2014 through 2016 growing seasons. Flower measurements and characteristics are from secondary flowers unless otherwise noted. Fruit characteristics and measurements are from secondary fruit unless otherwise noted.

Color references are made to The Royal Horticultural Society Colour Chart (R.H.S.), except where general colors of ordinary significance are used. Color values were taken under daylight conditions at approximately noon in San Giuseppe di Comacchio, Ferrara, Italy. The approximate age of the observed plants is about 7 months.

The following tables 3-9 describe fruit, plant, stolon, foliage, fruiting truss, flower and pest/disease characteristics of the new strawberry 'CIVN260'.

TABLE 3

| FRUIT CHARACTERISTICS | |
|---|---|
| Characteristic | 'CIVN260' |
| Color of mature fruit | Red group—RHS 44A |
| Color of internal flesh | Red group—RHS 42B |
| Length (cm) | 5 cm |
| Width (cm) | 3.5 cm |
| Ratio length/width | Moderately longer |
| Calyx diameter (cm) | 1.5 cm |
| Average weight (gm) | 20 gm |
| Achene color | Yellow-green group—RHS 151A |
| Number of achenes per $cm^2$ measured at the center of berry | About 10 |
| Average weight of 1000 achenes (g) | About 0.62 |
| Marketable yield (gm/plt) | Average 834 gm/plt |
| Size | Large |
| Predominant shape | Conical |
| Difference in shapes between primary and secondary fruit | Slight |
| Band without achenes | Medium |
| Unevenness of surface | Weak |
| Evenness of color | Even or very slight uneven |
| Glossiness | Medium |
| Insertion of achenes | Below surface |
| Insertion of calyx | Slightly raised |
| Attitude of the calyx | Outwards |
| Size of calyx in relation to fruit diameter | Some size or slightly large |
| Adherence of calyx | Strong |
| Firmness of skin | Firm |
| Firmness of flesh | Firm |
| Distribution of red color of the flesh | Uniform |
| Hollow center expression | Absent or small |
| Flavor | Good taste with good aroma and sugar content |
| Soluble solids (% brix) | 9° |
| Time of first flowering | 28 Mar. 2016 in San Giuseppe di Comacchio, Ferrara, Italy |
| Time of first harvesting | Very early to early |
| Harvest period | April to June in San Giuseppe di Comacchio, Ferrara, Italy |
| Type of bearing | Not remontant |

TABLE 4

| PLANT CHARACTERISTICS | |
|---|---|
| Characteristic | 'CIVN260' |
| Height (cm) | About 35 to 40 cm |
| Spread (cm) | About 50 cm |
| Size | Large |
| Habit | Upright |
| Density | Medium |
| Vigor | Medium to strong |

TABLE 5

| STOLON CHARACTERISTICS | |
|---|---|
| Characteristic | 'CIVN260' |
| Average number per plant | 8-12 |
| Anthocyanin coloration | Red group—RHS 53B |
| Anthocyanin intensity | Very low |
| Diameter at bract (mm) | 3 mm |
| Pubescence | Low |

TABLE 6

| FOLIAGE CHARACTERISTICS | |
|---|---|
| Characteristic | 'CIVN260' |
| Foliage: | |
| Color of upper surface | Green group—RHS 137A |
| Color of underside | Green group—RHS 137C |
| Shape in cross section | Concave |
| Interveinal blistering | Medium |
| Glossiness | Weak |
| Number of leaflets | 3 only |
| Terminal Leaflet: | |
| Length (cm) | About 12.5 cm |
| Width (cm) | About 10 cm |
| Length/width ratio | Moderately longer |
| Serrations/leaf | Overlapping |
| Size | Big |
| Shape of base | Obtuse |
| Shape of teeth | Serrate to crenate |
| Petiole: | |
| Length (cm) | About 30 cm |
| Diameter (mm) | About 4 mm |
| Pubescence | Weak |
| Attitude of hairs | Slightly outwards |
| Stipule: | |
| Length (mm) | About 15 mm |
| Width (mm) | About 5/6 mm at the base |
| Anthocyanin coloration | Weak |
| Color | Yellow-green group—RHS 145A |

TABLE 7

| FRUITING TRUSS CHARACTERISTICS | |
|---|---|
| Characteristic | 'CIVN260' |
| Length (cm) | About 30 to 35 cm |
| Attitude | Erect |
| Position relative to foliage | Slightly down |
| Pubescence | Medium |
| Anthocyanin intensity | Absent or very low |
| Attitude at first pick | From 45° to horizontal |

TABLE 8

| FLOWER CHARACTERISTICS | |
|---|---|
| Characteristic | 'CIVN260' |
| Petal color | |
| Mature (upper) | White group—RHS 155D |
| Mature (lower) | White group—RHS 155D |
| Petal shape | |
| Overall | Round |
| Apex | Rounded |
| Base | Rounded |
| Petal length (mm) | 10 mm |
| Petal width (mm) | 10 mm |
| Petal length/width ratio | Equal |
| Number of petals/flower | About 6 |
| Sepals color | |
| Mature (upper) | Green group—RHS 142A |
| Mature (lower) | Green group—RHS 138C |
| Sepal shape | |
| Overall | Lancelolate |
| Apex | Pointed |
| Base | Flat |
| Sepal length (mm) | About 10 mm |
| Sepal width (mm) | About 5/6 mm |
| Sepal length/width ratio | Longer |
| Number of sepals/flower | About 12 to 14 |
| Corolla diameter (mm) | About 30 mm |
| Calyx diameter (mm) | About 27 mm |
| Size of calyx relative to corolla | Smaller |
| Size of inner calyx relative to outer calyx | Some size |
| Relative position of petals | Free to touching |

TABLE 9

| PEST AND DISEASE REACTIONS |
|---|
| 'CIVN260' shows high resistance to powdery mildew and generally to leaf and root diseases. |

We claim:

1. A new and distinct variety of strawberry plant named 'CIVN260', as herein described and illustrated by the characteristics set forth above.

* * * * *